United States Patent [19]

Sanchez

[11] 4,008,728
[45] Feb. 22, 1977

[54] DENTAL FLOSS HOLDERS
[75] Inventor: Nicolas S. Sanchez, Vancouver, Canada
[73] Assignee: Raymond Lee Organization Inc., a part interest
[22] Filed: May 27, 1975
[21] Appl. No.: 580,807
[52] U.S. Cl. ............................................. 132/92 R
[51] Int. Cl.² .......................................... A61C 15/00
[58] Field of Search ................... 132/91, 89, 90, 92

[56] References Cited
UNITED STATES PATENTS

| | | | |
|---|---|---|---|
| 1,582,000 | 4/1926 | Gesell | 132/92 R |
| 1,724,516 | 8/1929 | Remedios | 132/84 D |
| 2,207,953 | 7/1940 | Summerbell | 132/91 |
| 2,233,936 | 3/1941 | Campbell | 132/92 A |
| 2,811,162 | 10/1957 | Brody | 132/89 |
| 3,885,579 | 5/1975 | Navrat | 132/92 R |

*Primary Examiner*—G.E. McNeill

[57] ABSTRACT

An elongated member has two like, forwardly, downwardly and outwardly extending prongs attached to its forward end slightly forward of an outwardly extending bore. In one embodiment, the member extends forwardly of a reservoir for receiving a spool of dental floss, and bears two opposed outwardly extending slotted posts. The forward end of each prong bears a hole, and a conventional dental floss cutter tab is disposed behind one post. In a second embodiment, the member and prongs are made of a flexible material, and the bore, posts, cutter and reservoir are omitted, with the hole in each prong being changed to a spiral slot.

4 Claims, 4 Drawing Figures

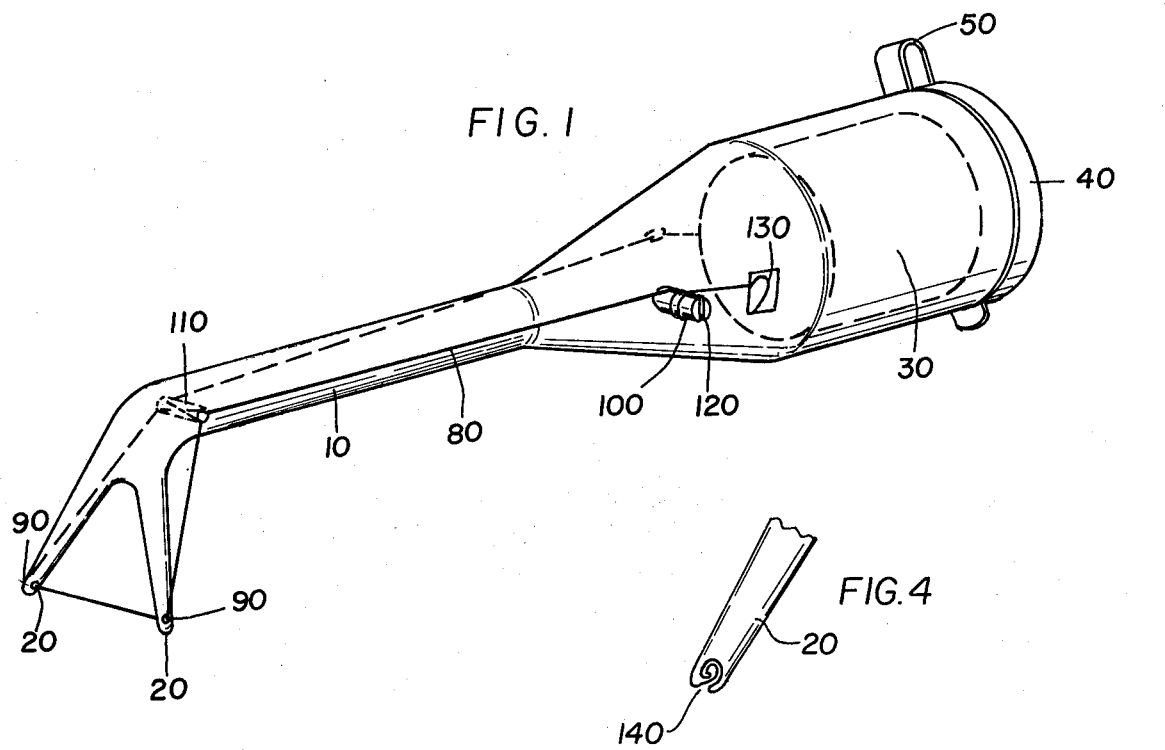
FIG. 1
FIG. 4
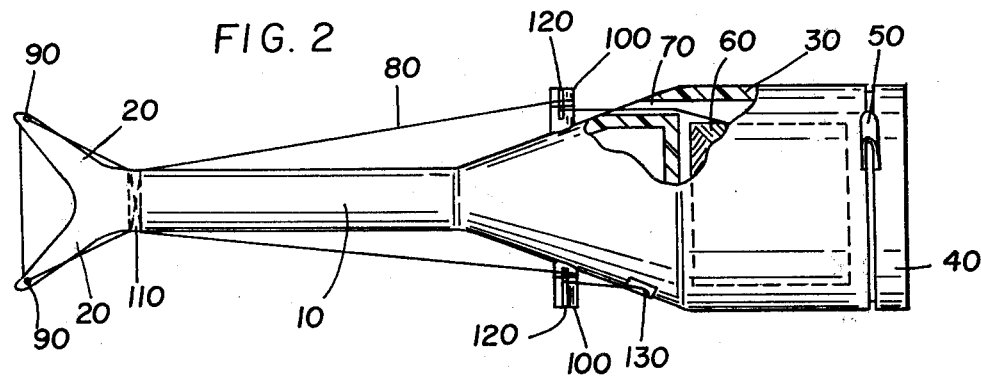
FIG. 2
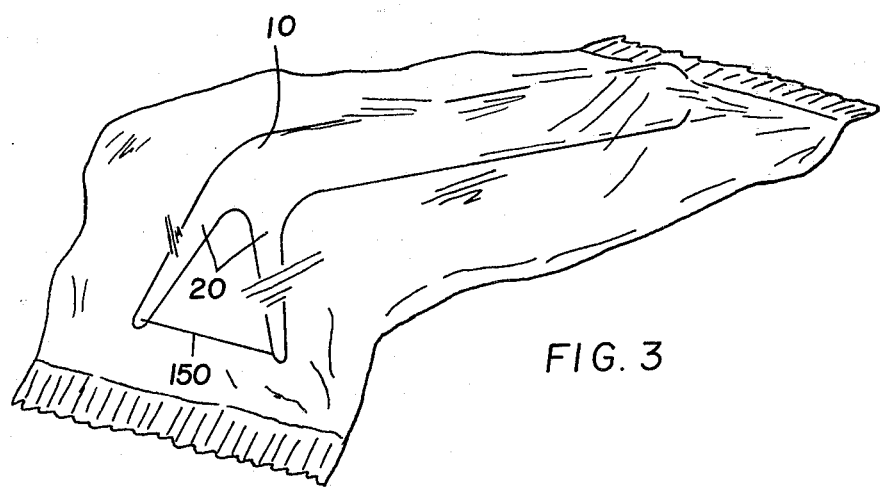
FIG. 3

DENTAL FLOSS HOLDERS

SUMMARY OF THE INVENTION

The invention is directed towards a device which can be used to stretch a length of dental floss taut, to enable a user to conveniently floss between his teeth without putting his fingers in his mouth.

Thus, an elongated member has two like, opposed, forwardly, downwardly and outwardly extending prongs attached to its forward end to form a V. The member and prongs are not coplanar. The floss is stretched taut between the tips of the prongs, to form a short length of exposed dental floss that can be used to floss the user's teeth.

BRIEF DESCRIPTION OF THE DRAWINGS

FIG. 1 is a drawing of the invention.

FIG. 2 is a top view of the invention partially cut away to show construction details.

FIG. 3 is a drawing of a second embodiment of the invention.

FIG. 4 is a detailed view of a portion of FIG. 3.

DETAILED DESCRIPTION OF THE PREFERRED EMBODIMENT

In both embodiments shown, an elongated member 10 has two like, opposed downwardly, forwardly and outwardly extending prongs 20 attached to its forward end.

In one embodiment shown in FIGS. 1 and 2, the member extends forwardly of a hollow cylindrical reservoir 30 with an open rear end. The rear end is closable by a circular cap 40 that is attached to the reservoir by a flexible plastic flap 50, and that snaps onto the rear end of the reservoir to seal a spool of dental floss 60 therein. A hole 70 extending out of the reservoir allows the floss 80 to be drawn off the spool.

The floss is eventually drawn through holes 90 in the tips of the prongs, to leave a short length of floss exposed for use. To keep the floss taut between the tips, two like outwardly extending opposed posts 100 cooperate with outwardly extending bore 110. The bore is disposed in the member just behind the prongs, and the posts are attached to the member forward of the reservoir. The posts end have a vertical slot 120. The floss, after emerging through hole 70, is passed through the slot in the post directly forward of the hole 70 in FIG. 2, and is then wrapped around that post. The floss is then passed through bore 110 to the opposite side of the member, then through the holes 90 to the side of the member on which the floss first emerged, and thence through the bore 110 again and through and around the remaining post. A conventional dental floss cutter tab 130 is disposed on the member behind this last post, to cut off used lengths of floss.

In the embodiment shown in FIGS. 3 and 4, the member and prongs are made of slightly flexible material, and the forward end of each prong bears a spiral slot 140. A short length of dental floss 150 which has knots at its ends is stretched between the prongs with the knots outside the spiral slots. Because the prongs are slightly further apart then the length of the floss, the prongs are bent slightly towards each other and the floss is kept stretched out.

Although the invention has been described with particular reference to the drawings, the protection sought is to be limited only by the terms of the claims which follow.

What is claimed is:

1. A dental floss holder comprising:
   an elongated member with forward and rearward ends and lying in a plane;
   first and second like prongs integral at one rearward end with the forward end of the member, the prongs being opposed and extending forwardly, downwardly and outwardly to form a V in a single plane that intersects the plane in which the member lies, each prong having a spiral slot in its forward end;
   a hollow, cylindrical reservoir extending rearwardly of the member and bearing a hole through which dental floss can be withdrawn from the interior of the reservoir;
   two like opposed outwardly extending post each having a vertical slot and each being attached to the member at points forwardly of the reservoir; and
   a spool of dental floss located in the reservoir, with the floss passing out of the hole in the reservoir, passing through the slot in each post and being wrapped around each post and passing through the holes in the prongs and extending between the prongs intermediate the wrapped portions.

2. The holder of claim 1 wherein said member adjacent said prongs has a transverse bore, said floss after passing each one of the posts passes through said transverse bore before passing to the holes in the prongs.

3. The holder of claim 2 wherein each one of the posts is disposed on the same side of the member as a corresponding prong and wherein there are two portions of the floss in the bore that cross each other.

4. The holder of claim 3 further including a conventional dental floss cutter tab attached to the member directly behind one of the posts.

* * * * *